United States Patent
Lau et al.

(10) Patent No.: US 7,357,033 B2
(45) Date of Patent: *Apr. 15, 2008

(54) MANUAL RESUSCITATORS WITH INTEGRAL MANOMETER

(75) Inventors: Gregory Lau, Mocksville, NC (US); Robert M. Martin, Jr., Hardy, VA (US)

(73) Assignee: Ventlab Corporation, Mocksville, NC (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/337,397

(22) Filed: Jan. 23, 2006

(65) Prior Publication Data

US 2006/0156823 A1     Jul. 20, 2006

Related U.S. Application Data

(62) Division of application No. 10/678,755, filed on Oct. 3, 2003, now Pat. No. 7,051,596.

(51) Int. Cl.
*G01L 13/02* (2006.01)
(52) U.S. Cl. .......................................... 73/736; 73/756
(58) Field of Classification Search .................. 73/716, 73/736, 700, 715, 744
See application file for complete search history.

(56) References Cited

U.S. PATENT DOCUMENTS

| | | | | |
|---|---|---|---|---|
| 2,271,286 A | 1/1942 | Longstreet | ..................... | 73/111 |
| 2,509,644 A | 5/1950 | Kinderman | ................... | 73/317 |
| 2,577,608 A | 12/1951 | Coultrip | ..................... | 73/715 |
| 2,701,968 A | 2/1955 | Brown | ......................... | 73/414 |
| 2,796,765 A | 6/1957 | Huston | | |
| 3,195,354 A | 7/1965 | Douslin | ..................... | 73/64.45 |
| 3,196,866 A | 7/1965 | Adams | ......................... | 128/29 |
| 3,260,118 A | 7/1966 | Dousolin | ..................... | 73/744 |
| 3,335,609 A | 8/1967 | Nelson | ......................... | 73/414 |
| 3,373,614 A | 3/1968 | Neyer | ......................... | 73/716 |
| 3,975,959 A | 8/1976 | Larkin | ......................... | 73/419 |
| 4,020,784 A | 5/1977 | Greene | ....................... | 116/114 |
| 4,040,298 A | 8/1977 | Lee et al. | ..................... | 73/406 |

(Continued)

FOREIGN PATENT DOCUMENTS

EP           139363           5/1985

(Continued)

OTHER PUBLICATIONS

Mercury Medical Products & Services information for resuscitators, resuscitators-manometers; information from the internet; copyright 2000.

(Continued)

*Primary Examiner*—Andre J. Allen
(74) *Attorney, Agent, or Firm*—MacCord Mason PLLC

(57) ABSTRACT

A manometer integrated into a manual resuscitator includes a housing with a communication path, and a pressure gauge integrally forming part of the housing. A sensing chamber and an atmospheric chamber are separated by a diaphragm subject to distortion by differential pressure between the chambers, with a spring to restore the diaphragm upon equalization of the pressures. A shaft journaled in a first bearing on the diaphragm and a second bearing in one of the chambers rotates in the bearings upon diaphragm distortion, and an indicator on the shaft indicates differences in pressure between the chambers.

3 Claims, 3 Drawing Sheets

U.S. PATENT DOCUMENTS

| | | | |
|---|---|---|---|
| 4,143,545 A | 3/1979 | Sitabkahm | 73/146.8 |
| 4,347,744 A | 9/1982 | Buchanan | 73/715 |
| 4,388,833 A | 6/1983 | Kuwayama | 73/718 |
| 4,433,579 A | 2/1984 | Horn | 73/715 |
| 4,685,336 A | 8/1987 | Lee | 73/715 |
| 4,811,730 A | 3/1989 | Milano | 128/203.11 |
| 4,821,713 A | 4/1989 | Bauman | 128/205.13 |
| 4,934,360 A | 6/1990 | Heilbron et al. | 128/205.16 |
| 4,945,918 A | 8/1990 | Abernathy | 128/719 |
| 5,109,840 A | 5/1992 | Daleiden | 128/205.13 |
| 5,116,088 A | 5/1992 | Bird | 285/319 |
| 5,140,982 A | 8/1992 | Bauman | 128/205.13 |
| 5,163,424 A | 11/1992 | Kohnke | 128/205.13 |
| 5,213,096 A | 5/1993 | Kihlberg et al. | 128/205.12 |
| 5,357,951 A | 10/1994 | Ratner | 128/205.24 |
| 5,557,049 A | 9/1996 | Ratner | 73/715 |
| 6,119,525 A | 9/2000 | Hamma | 73/739 |
| D436,050 S | 1/2001 | Ratmer | D10/94 |
| 6,672,171 B2 * | 1/2004 | Gu et al. | 73/724 |
| 6,813,964 B1 * | 11/2004 | Clark et al. | 73/861.52 |
| 6,964,204 B2 * | 11/2005 | Clark et al. | 73/861.52 |
| 7,051,596 B1 * | 5/2006 | Lau et al. | 73/716 |
| 7,082,843 B2 * | 8/2006 | Clark et al. | 73/861.53 |

FOREIGN PATENT DOCUMENTS

| | | |
|---|---|---|
| GB | 910065 | 11/1962 |
| GB | 2139099 | 11/1984 |

OTHER PUBLICATIONS

Mercury Manufactured Products Mamometer information from the internet; copyright 2000.

Ventlab Corporation PT valve w/pressure gauge diagram; Aug. 2001.

Lighten Stone Corporation Dwyer Series Magnahelic Differential Pressure Gauge; undated, admitted prior art.

Definition of passageway taken from Dictionary.com; undated; admitted prior art.

The Mercury CPR Bag; A single-patient -use manual resuscitator; undated, admitted prior art.

* cited by examiner

MANUAL RESUSCITATORS WITH INTEGRAL MANOMETER

This application is a division of utility application Ser. No. 10/678,755 filed Oct. 3, 2003 and now U.S. Pat. No. 7,051,596.

BACKGROUND OF THE INVENTION

The present invention involves a manometer that is integrated into a fitting on manual resuscitators, such as a patient valve or a hyperinflation elbow.

Manual resuscitators typically are either self-inflating or flow dependent. In either instance, a significant component of a manual resuscitator is a flexible air bag. The air bag varies in size depending on the intended patient—infant, child, or adult. The air bag is typically connected to an oxygen supply, although self-inflating manometers can operate without such supplemental oxygen. The air bag is further connected to a fitting, wherein the fitting directs airflow into a patient, typically through a mask or endotracheal tube. Manometers have been connected to fittings in the past to measure the air pressure being directed towards the patient. Some manometers are also able to measure the patient's expiratory pressure. The manometer is installed "in line" with the air flow, so that a portion of the air flow can be directed into the manometer to be measured.

Known manometer installations for similar bags are as seen U.S. Pat. Nos. D436,050 to Ratner entitled "Hyper inflation bag attached to a manometer;" U.S. Pat. No. 5,357,951 to Ratner entitled "Cardiac pulmonary resuscitator apparatus valve with integral air sampling port;" and U.S. Pat. No. 5,557,049 to Ratner entitled "Disposable manometer for use with a CPR bag." These manometers have the common characteristic of being separable from the valve, which results in the need to manufacture two elements to combine to together, raising manufacturing costs. Their separate characteristics also risk the separation of the elements, resulting in possible inoperability or reduced functionality at the time the combination is needed most.

SUMMARY OF THE INVENTION

The present invention overcomes one or more of these shortcomings by providing a resuscitator for a patient breathing apparatus including a housing having an inlet and outlet connected by a communication path. In some cases a check valve permits air flow through the communication path only from the inlet to the outlet. A pressure gauge forming part of the housing has a sensing chamber in communication with the communication path and an atmospheric chamber in communication with ambient atmosphere. The chambers are separated by a diaphragm subject to distortion from a rest position upon a differential pressure between the chambers, and a spring associated with the diaphragm restores the diaphragm to the rest position upon equalization of the pressures in the chambers. A shaft is journaled in a first bearing attached to the diaphragm and a second bearing in one of the chambers for rotation in one direction upon diaphragm distortion and rotation in another direction by diaphragm restoration. An indicator associated with the shaft indicates differences in pressure between the sensing and atmospheric chambers that cause diaphragm distortion.

In a preferred embodiment, the sensing chamber is below the atmospheric chamber, and the indicator is in the atmospheric chamber. Alternatively, the indicator may be in the sensing chamber. The atmospheric chamber may include a transparent window, with the indicator in the atmospheric chamber and including a dial in the atmospheric chamber visible through the window and a pointer on the shaft. The atmospheric chamber may enclose the spring and the second bearing.

In a preferred embodiment the housing and the pressure gauge are formed of plastic ultrasonically welded together.

The pressure gauge may have a lower housing part extending toward either the inlet or the outlet and having circumferentially arranged crescent-shaped openings to establish communication between the sensing chamber and the communication path.

The sensing chamber may include a sleeve aligned with the first bearing and positioned to receive the shaft when the diaphragm is distorted by a pressure differential. If so, the first bearing may have an aperture with an outward notch, and the shaft may have a helical thread adapted to ride in the notch and rotate the shaft as the first bearing moves with diaphragm distortion.

The pressure gauge may include a lower housing part extending toward the outlet, with the sensing chamber including a first sleeve aligned with the first bearing for receiving the shaft when the diaphragm is distorted by a pressure differential and a second sleeve on the lower housing part to maintain alignment of the first sleeve.

The invention can also be considered as a resuscitator having an inlet and outlet connected by a communication path and a pressure sensing means for sensing a pressure in the communication path, the pressure sensing means being integral with the housing to the extent of not being separable from the housing without damage to the housing or sensing means.

The invention may also be considered as a patient breathing apparatus including a housing having an inlet and outlet for respiratory air connected by a communication path; and a pressure sensing means for sensing a pressure in the communication path, the pressure sensing means being integral with the housing to the extent of not being separable from the housing without damage to the housing or sensing means.

The invention may also be considered as a method of providing respiratory assistance to a patient including supplying air to the patient through a housing having an inlet and outlet connected by a communication path; and displaying the pressure of supplied air in the housing on a pressure gauge forming an integral part of the housing by distorting a diaphragm from a rest position upon a differential pressure between two chambers in the housing and restoring the diaphragm to the rest position upon equalization of the pressures in the chambers, thereby moving an indicator coupled to the diaphragm to indicate differences in pressure between the chambers.

BRIEF DESCRIPTION OF THE DRAWINGS

The invention will be better understood by a reading of the Detailed Description of the Examples of the Invention along with a review of the drawings, in which.

DETAILED DESCRIPTION OF EXAMPLES OF THE INVENTION

Figure 1:
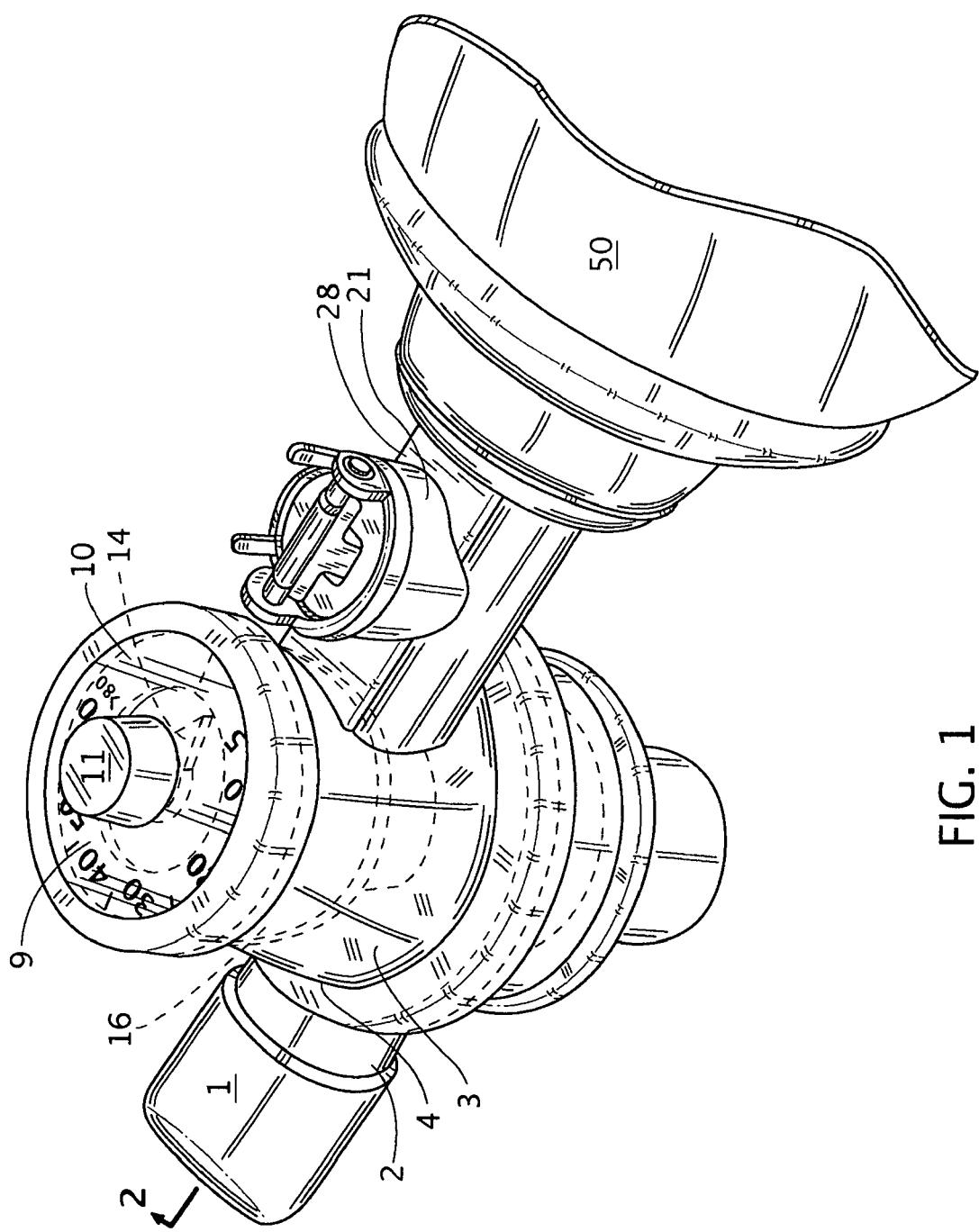
FIG. 1 is a perspective view of the resuscitator with an integral manometer.
Figure 2:
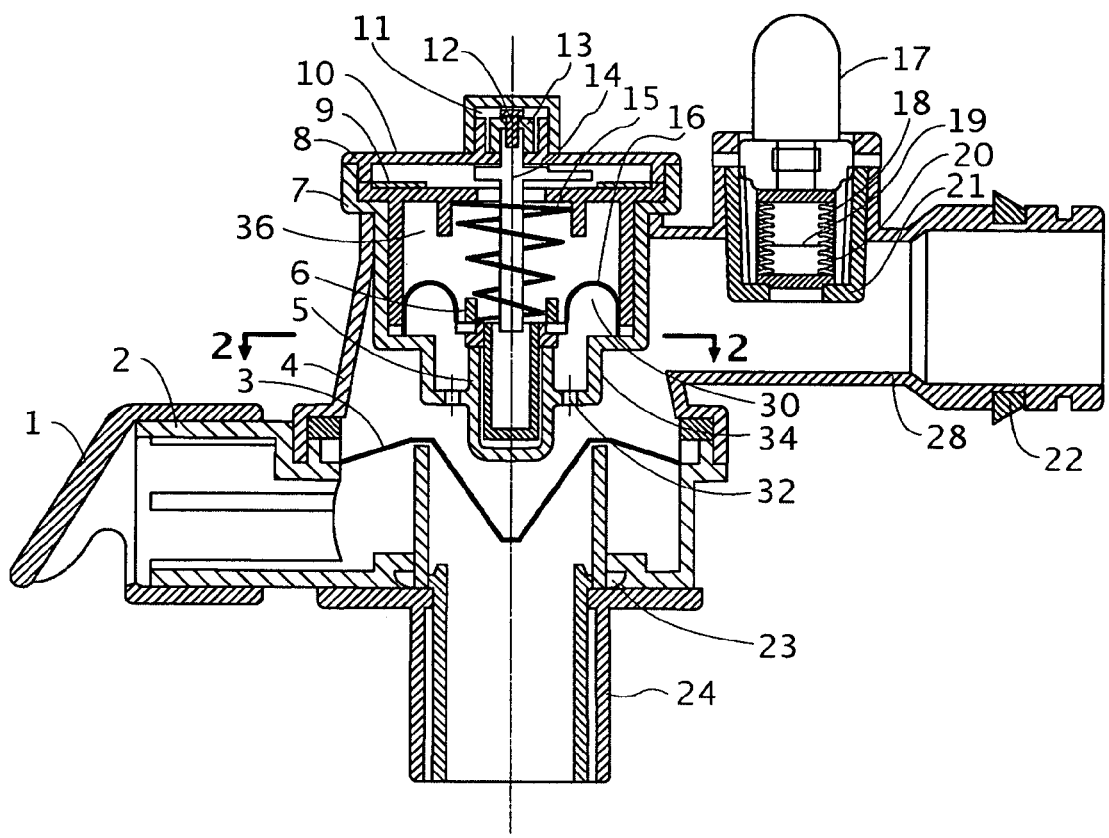
FIG. 2 is a sectional view of the embodiment of FIG. 1 taken along lines 2-2 and looking in the direction of the arrows.

As seen in FIG. 1, a resuscitator with integral manometer is connected with a squeezable air bag 50 in conventional fashion. The air bag is connected with the resuscitator and manometer housing. As seen in FIGS. 1 and 2, the housing is made up of a neck 28 providing an inlet communicating with an outlet or patient port 24 and establishing a communication path between the inlet and outlet. A check valve is established by a conventional duck-bill valve 3. In other embodiments the check valve is omitted. In this particular embodiment, an expiration diverter 2 covered by a diverter cap 1 receives exhalation flow from the patient port 24 as the patient exhales and the path back to the inlet 28 is blocked by the duck-bill valve 3.

In conventional fashion, a pop-off housing 21 can be provided, but such a housing is not material to the present invention.

Figure 3:
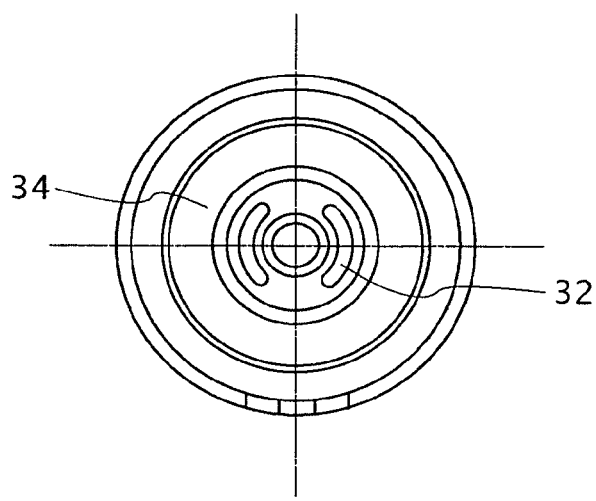
FIG. 3 is a view of the lower housing part.

Integrally formed to communicate with the communication path between the inlet 28 and the patient port 24 is a pressure gauge in the form of a manometer, viewed in better detail in FIG. 2. The manometer includes a housing 4, and a main body 7 having at a lower end thereof a lower housing part 34 having inlets 32 communicating air from the air communication path into the interior of the lower housing part 34. Such holes 32 can best seen in FIG. 3 as crescent shaped openings.

The housing is divided into a sensing chamber 30 and an atmospheric chamber 36 by a diaphragm 16. Mounted interiorly of the diaphragm 16 is a helix guide or bearing 6 at the top of end of a helix housing 5, which is fashioned as a sleeve. An additional outer sleeve formed integrally with the lower housing part 34 provides guidance for the movement of the helix housing 5, which is freely moveable in the outer sleeve driven by movement of the diaphragm and the helix guide 6, to which it is affixed.

An opening in the helix guide 6 receives the helix shaft 14, and the helical threading on the outer side of the pointer 14 rides in a notch in the helix guide 6, so that the upward movement of the helix guide 6 causes rotation of the pointer as the helix rides in the notch in the helix guide 6.

The atmospheric chamber 36 encloses a spring 15 centrally mounted between the helix guide 6 and the bottom of an inner cover 8. Note that the atmospheric chamber 36 is open to ambient atmosphere through any suitable opening, not seen in FIG. 2. A pivot or bearing 13 at the top of the atmospheric chamber 36 is held in place in a transparent cover 10 and has journaled in a bearing in the helical shaft 14. The helical shaft 14 has a pointer in the space between the inner cover 8 and the transparent cover 10. Also in that space, a scale plate 9 is provided to show numeric renditions of varying pressures which may be encountered upon the deflection of the diaphragm 16 by differential pressures between the sensing chamber 34 and the atmospheric chamber 36.

As can be seen, the main body 7 and the other associated components of the pressure gauge or manometer close off a hole that would otherwise be present in the housing 4. That is, the housing 4 would be inoperable to reliably transmit air from the inlet 28 to the patient port 24 without the manometer in place. In the preferred embodiment, the manometer is permanently affixed to the housing 4, such as by ultrasonic welding, to permanently close that opening. The result is an integral mounting. "Integral mounting" is meant herein that the attempted separation of the manometer from the resuscitator would cause damage to one or the other of the two, so that it would no longer be operable for its intended purpose. Such integral connections can be made in various ways including ultrasonic welding, adhesive mounting, integral injection molding or the like.

In operation, the patient port 24 can be affixed to a mask to be applied to the patient and the inlet 28 is affixed to a squeezable bag 50 or other respiratory air or oxygen source, so that the respiratory air is fed through the inlet 28 and passes through the check valve 3 to the patient for inhalation. As the patient exhales, the check valve 3 prevents return flow to the inlet 28 and also lifts, opening a path to the diverter 2, so the exhaled air is diverted through the diverter 2.

During the aforesaid steps, the pressure in the pathway between the inlet 28 and the patient port 24 can be measured. The pressure in that pathway is also present in the sensing chamber 34 because of the holes 32. If that pressure exceeds atmospheric pressure, a net force on the diaphragm 16 causes the diaphragm to flex upwardly in the view of FIG. 2, carrying the helix guide 6 together with the helix housing 5, resulting in the rotation of the pointer 14. Rotation of pointer 14 can be seen through the transparent cover 10: numbers on the scale 9 align with the pointer and give an indication of the degree of deflection of the diaphragm. This action is in opposition to the spring 15. Those of ordinary skill in the art can adequately calibrate a scale plate 9 to reflect the actual pressure differential between the sensing chamber 30 and the atmospheric chamber 36. As noted, because the atmospheric chamber 36 is open to atmosphere, the pressure there essentially never changes for the purposes of these measurements; the differential between atmospheric pressure and that in the sensing chamber 30 gives rise to the movement of the pointer 14 for visual indication. When the pressure in the chamber 30 subsides, the spring 15 restores the helical guide downwardly, with the helix housing 5 retracting into the sleeve component of the lower housing part, and the pressure sensing pointer returns to a zero differential pressure indication.

Because the pressure gauge is integral with the apparatus, manufacturing efficiencies are encountered, yielding a low manufacturing cost. Also the integral manometer cannot get disassembled or lost to disable the combination.

Figure 4:
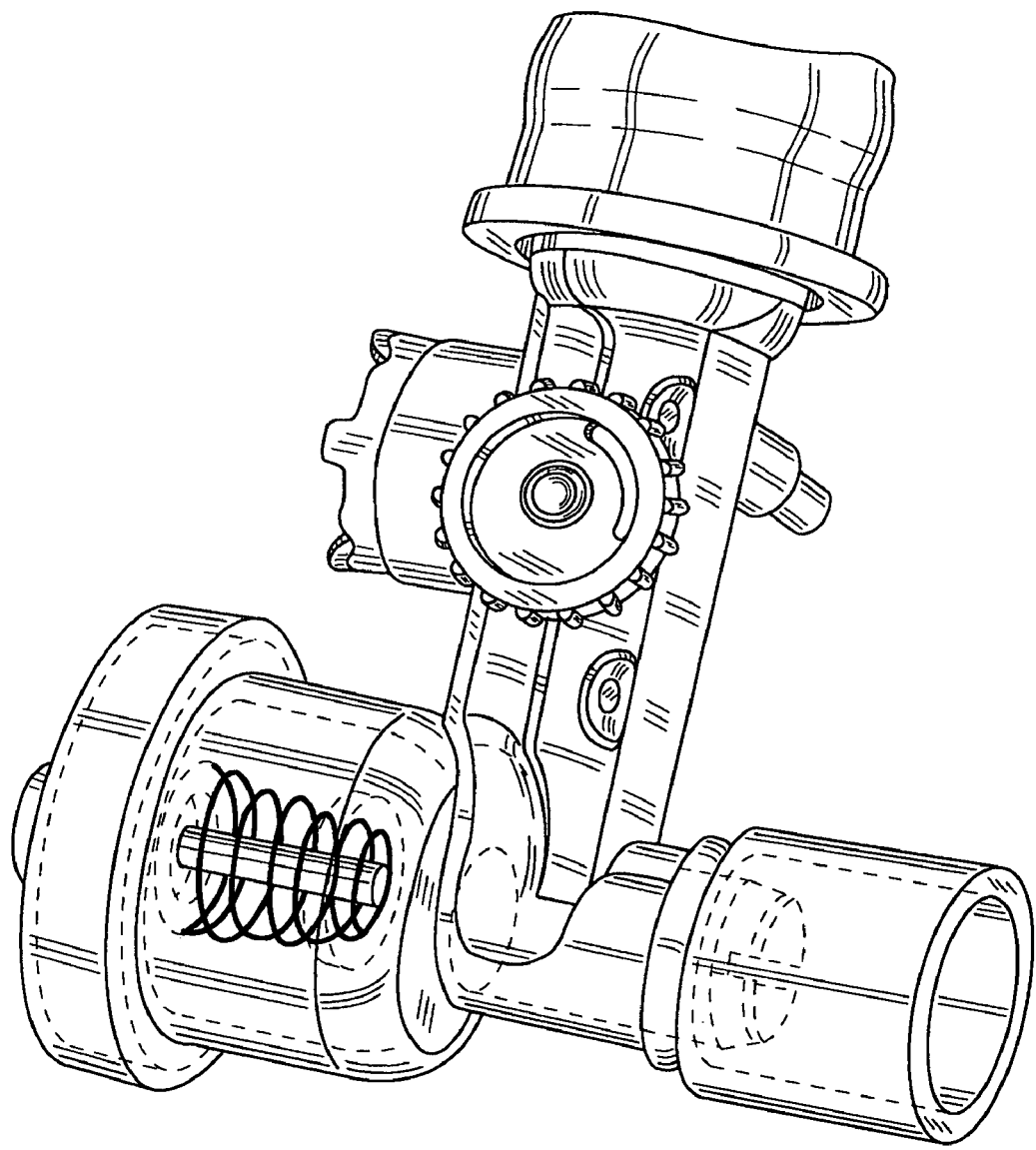
FIG. 4 is a perspective view of the integral manometer in another patient breathing tube.

FIG. 4 is a perspective view of another resuscitator with an integral manometer, in this case a hyperinflation elbow.

The invention is usable on numerous forms of patient breathing apparatuses including manual resuscitators of the self inflating and non self inflating type, hyper inflation systems, elbows and the like.

Certain modifications and improvements will occur to those skilled in the art upon reading the foregoing description. It should be understood that all such modifications and improvements have been omitted for the sake of conciseness and readability, but are properly within the scope of the following claims. For example, the positions of the atmospheric and sensing chambers may be reversed, with a pathway for the air to be sensed communicating with the sensing chamber. The spring may be positioned differently, such as being located in the sensing chamber as an extension spring instead of a compression spring (or vice versa if the chambers are reversed, as mentioned) or omitted altogether if the diaphragm has resilience to restore itself. Other types of indicators may be used, such as gear linkages to other readouts, or the like. The helical protrusion and notch arrangement can be reversed—the protrusion being an inward protrusion on the lumen of the bearing, riding in a helical groove on the shaft.

Other types of fluids can be introduced, such as relatively pure oxygen, through supplemental inlets at the inlet, or the pressure can be regulated with bleed valves or the like, known in the art.

What is claimed is:

1. A patient breathing apparatus comprising:
   a housing having an inlet and outlet configured to communicate respiratory air and connected by a communication path; and
   a pressure sensing means for sensing a pressure in the communication path, the pressure sensing means being integrally mounted with the housing to the extent of not being separable from the housing without damage to the housing or sensing means.

2. A method of providing breathing assistance to a patient comprising:
   supplying breathing air to the patient through a housing having an inlet and outlet connected by a communication path; and
   displaying the pressure of supplied air in the housing on a pressure gauge integrally mounted to the housing by distorting a diaphragm from a rest position upon a differential pressure between two chambers in the housing and restoring the diaphragm to the rest position upon equalization of the pressures in the chambers, thereby moving an indicator coupled to the diaphragm to indicate differences in pressure between the chambers.

3. A manual resuscitator apparatus comprising
   a housing having an inlet and outlet connected by a communication path and a valve means operably associated with the communication path; and
   a pressure sensing means for sensing a pressure in the communication path, the pressure sensing means being integrally mounted with the housing to the extent of not being separable from the housing without damage to the housing or sensing means.

* * * * *